US00PP22429P3

(12) United States Plant Patent
Zaiger et al.

(10) Patent No.: US PP22,429 P3
(45) Date of Patent: Jan. 3, 2012

(54) INTERSPECIFIC TREE NAMED 'BELLA ROSE'

(50) Latin Name: **Interspecific *Prunus* species**
Varietal Denomination: Bella Rose

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 214 days.

(21) Appl. No.: 12/657,441

(22) Filed: Jan. 21, 2010

(65) Prior Publication Data

US 2011/0179532 P1 Jul. 21, 2011

(51) Int. Cl.
*A01H 5/00* (2006.01)

(52) U.S. Cl. ..... Plt./180

(58) Field of Classification Search ..... Plt./180
See application file for complete search history.

(56) References Cited

U.S. PATENT DOCUMENTS

| | | | | | |
|---|---|---|---|---|---|
| PP111 | P | * | 11/1934 | Thompson | Plt./184 |
| PP2,539 | P | * | 6/1965 | Anderson | Plt./184 |
| PP2,877 | P | * | 4/1969 | Anderson | Plt./186 |
| PP19,834 | P2 | * | 3/2009 | Zaiger et al. | Plt./180 |

OTHER PUBLICATIONS

UPOV ROM GTITM Computer Database GTI Jouve Retrieval Software 2011/01 Citation for 'Bella Rose'.*

* cited by examiner

*Primary Examiner* — Wendy C Haas

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular production of medium size fruit.
2. Fruit with good flavor and eating quality.
3. Fruit with an attractive red skin color.
4. The tree being approximately ½ the height and width of standard commercial fruit trees.
5. Fruit with good storage and shelf life.

1 Drawing Sheet

Botanical classification: Interspecific *Prunus* species.
Variety denomination: 'Bella Rose'.

BACKGROUND OF THE VARIETY

Field of the Invention

In the field of plant genetics, we conduct an extensive and continuing plant-breeding program including the organization and asexual reproduction of orchard trees, of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum, apricot and interspecific trees which are known to us and mentioned herein, 'Mariposa' Plum (U.S. Plant Pat. No. 111), 'Red Beaut' Plum (U.S. Plant Pat. No. 2,539), 'Patterson' Apricot (U.S. Plant Pat. No. 2,877) and the proprietary interspecific trees '288LF475' (unpatented), '57EF372' (unpatented) and '10W100' (unpatented).

STATEMENT REGARDING FEDERALLY SPONSORED RESEARCH AND DEVELOPMENT

Not applicable.

ORIGIN OF THE VARIETY

The present new variety of interspecific tree was originated by us from crosses between the following species: [*Prunus salicina*×(*Prunus salicina*×*Prunus armeniaca*)]×[*Prunus armeniaca*×(*Prunus persica*×*Prunus armeniaca*)]. The present variety was selected from a first generation cross between the proprietary selected interspecific seedlings '288LF475' and '57EF372'. The seed parent '288LF475' was developed by us from multiple crosses between the following varieties, 'Mariposa' Plum (U.S. Plant Pat. No. 111) and 'Red Beaut' Plum (U.S. Plant Pat. No. 2,539) crossed with a proprietary apricot of unknown parentage. The pollen parent '57EF372' was selected by us from a cross between 'Patterson' Apricot (U.S. Plant Pat. No. 2,877) and the proprietary peachcot selection '10W100'. We budded a large number of these first generation seedlings to older 'Nemaguard' Rootstock (non-patented) trees to induce earlier fruit production for evaluation. Under close observation, one seedling, which is the present variety, exhibited desirable fruit and tree characteristics, and was selected in 1997 for additional asexual propagation and commercialization.

ASEXUAL REPRODUCION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree [(Plum×Plumcot)×(Cot×Peachcot)] is small to medium in size, upright in growth and a productive and regular bearer of medium size fruit with good flavor and eating quality. The fruit is further characterized by having an attractive red skin color, being semi-freestone with light yellow, firm flesh with good storage and shipping quality. In comparison to its seed parent (288LF475), the skin of the new interspecific variety has pubescence compared to smooth slick skin. The fruit is approximately 30 days earlier in maturity and the tree is approximately ½ the height and width in tree structure. In comparison to its pollen parent (57EF372), the fruit of the new variety has red skin, compared to yellow, is approximately 19 days earlier in maturity and the tree is approximately ½ the height and width in structure. Both parents are standard commercial size trees.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 12 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 12 year old specimens grown near Modesto, Calif., with color in accordance with Munsell Book of Color.

Tree:

*Size.*—Small, pruned to 1.5 to 2 meters in height and 2 meters in width, varies with cultural practices.

*Vigor.*—Low to medium. Growth of one meter in height and width the first growing season.

*Form.*—Upright, usually pruned to vase shape to allow more sunlight to center of tree to enhance fruit color and health of fruit spurs.

*Branching habit.*—Upright, crotch angle approximately 30°, increases with heavy crop load.

*Productivity.*—Productive, thinning and spacing desired for commercial size fruit. Fruit set varies with climatic conditions at bloom time.

*Bearer.*—Regular, adequate fruit set for 9 consecutive years, no alternate bearing observed.

*Fertility.*—Self sterile, pollinator required.

*Density.*—Medium dense, controlled by pruning.

*Hardiness.*—Hardy in all stone fruit growing areas of California. Tree grown in USDA Hardiness Zone 9. Winter chilling requirement approximately 800 hours at or below 45° F.

Trunk:

*Size.*—Small to medium. Average circumference 25.4 cm at 25.6 cm above ground.

*Stocky.*—Medium.

*Texture.*—Medium shaggy, roughness increases with age of tree.

*Color.*—Varies from 2.5Y 6/2 to 2.5Y 3/2.

Branches:

*Size.*—Small to medium. Average circumference 13.2 cm at 1 meter above ground.

*Surface texture.*—New growth relatively smooth. Mature growth medium rough, roughness increases with age.

*Lenticels.*—Average number 46 in a 25.8 sq cm surface of branch. Average length 1.6 mm. Average width 0.8 mm. Color varies from 10YR 6/8 to 10YR 6/10.

*Color.*—New growth varies from 5GY 5/8 to 10YR 4/6. Mature growth varies from 7.5YR 3/4 to 10YR 3/6., varies with age of growth.

Leaves:

*Size.*—Large. Average length 107.8 mm. Average width 48.1 mm.

*Form.*—Elliptic.

*Apex.*—Cuspidate.

*Base.*—Cuneate.

*Margin.*—Serrulate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Average length 38.8 mm. Average width 1.4 mm. Color varies from 2.5GY 8/6 to 5R 2/8. Longitudinally grooved. Surface — glabrous.

*Glands.*—Type — globose. Size — small. Average length 0.5 mm. Average diameter 0.4 mm. Average number 2, varies from 1 to 4. Located primarily on upper portion of petiole and base of leaf blade. Color varies from 5GY 6/8 to 5R 2/8.

*Stipules.*—Average number 2. Average length 7.7 mm. Edges serrulate. Color varies from 2.5GY 7/6 to 5GY 7/8.

*Color.*—Upper surface varies from 7.5GY 3/2 to 7.5GY 2/2. Lower surface varies from 5GY 3/4 to 7.5GY 3/4. Midrib color varies from 2.5GY 5/4 to 2.5GY 5/6.

Flower buds:

*Size.*—Medium. Average length 14.3 mm. Average diameter 7.0 mm.

*Hardiness.*—Hardy in all stone fruit growing areas of California.

*Form.*—Conical, becomes elongated just before opening.

*Pedicel.*—Average length 6.6 mm. Average width 0.6 mm. Color varies from 2.5Y 6/8 to 5GY 6/6.

*Color.*—N 9.5/(white).

*Number of buds per spur.*—Average number 15, varies from 7 to 18.

Flowers:

*Blooming period.*—Date of First Bloom Feb. 21, 2009. Date of Petal Fall Mar. 1, 2009, varies slightly with climatic conditions.

*Size.*—Medium to large. Average height 16.2 mm. Average diameter 28.2 mm.

*Petals.*—Number — normally 5, varies from 5 to 10, alternately arranged to sepals. Average length 13.6 mm. Average width 14.5 mm. Form — orbicular. Margin — sinuate. Color — N 9.5/(white). Both surfaces glabrous.

*Sepals.*—Number — normally 5, varying from 5 to 10, alternately arranged to petals. Size — medium. Average length 4.2 mm. Average width 3.9 mm. Shape — triangular, apex rounded. Margin — entire. Upper surface glabrous, lower surface pubescent. Color — upper surface varies from 5GY 5/6 to 2.5R 3/6. Lower surface varies from 5GY 5/8 to 2.5R 3/6.

*Stamens.*—Average number per flower 37. Average filament length 12.2 mm. Filament color N 9.5/(white). Anther color varies from 5Y 8/8 to 5Y 8/10.

*Pollen.*—Self sterile, pollinator required. Abundant, pollen sacs full. Color varies from 2.5Y 7/10 to 5Y 7/10.

*Pistil.*—Normally 1, varies from 1 to 3. Surface — pubescent. Average length 13.2 mm. Position of stigma average of 1.2 mm below anthers. Color varies from 2.5GY 8/6 to 2.5GY 8/8.

*Fragrance.*—Moderate to heavy aroma.

*Color.*—N 9.5/(white).

*Number flowers per flower bud.*—Average 2, varies from 1 to 4.

*Pedicel.*—Average length 6.9 mm. Average width 0.9 mm. Color varies from 2.5GY 7/8 to 5GY 7/6.

Fruit:

*Maturity when described.*—Firm ripe.

*Date of first picking.*—Jun. 20, 2009.

*Date of last picking.*—Jul. 5, 2009, varies with climatic conditions.

*Size.*—Medium. Average diameter axially 58.6 mm. Average transversely in suture plane 54.4 mm. Average weight 99.4 grams, varies slightly with fertility of the soil, amount of thinning and climatic conditions.

*Form.*—Slightly elongated.

*Suture.*—Very slightly lipped, extends from base to apex.

*Ventral surface.*—Nearly smooth, very slightly lipped.

*Apex.*—Nearly rounded to slight tip.

*Base.*—Varies from flat to slightly retuse.

*Stem cavity.*—Rounded to slightly elongated in suture plane. Average depth 3.9 mm. Average diameter 5.4 mm.

Stem:

*Size.*—Small to medium. Average length 15.3 mm. Average diameter 2.3 mm.

*Color.*—2.5Y 4/6.

Flesh:

*Ripens.*—Evenly.

*Texture.*—Firm, smooth.

*Fibers.*—Few, very small, tender.

*Firmness.*—Firm, much firmer than most commercial apricots.

*Aroma.*—Moderate.

*Amydgalin.*—Undetected.

*Eating quality.*—Good.

*Flavor.*—Good, with a good balance between sugar and acid.

*Juice.*—Heavy, enhances flavor.

*Brix.*—Average 16.7°, varies slightly with amount of fruit per tree and climatic conditions.

*Color.*—Varies from 2.5Y 8/10 to 2.5YR 5/14.

*Size of pit cavity.*—Average length 44.7 mm. Average width 21.9 mm. Color varies from 2.5Y 8/10 to 2.5YR 4/10.

Skin:

*Thickness.*—Medium.

*Surface.*—Smooth.

*Pubescence.*—Moderate amount, very short.

*Tendency to crack.*—None.

*Color.*—Ground color yellow, varies from 2.5Y 8/10 to 10YR 8/10. Overspread with red, varies from 5R 6/10 to 2.5R 2/8.

*Tenacity.*—Tenacious to flesh.

*Astringency.*—None.

Stone:

*Type.*—Semi-freestone.

*Size.*—Large. Average length 32.7 mm. Average width 19.9 mm. Average thickness 11.2 mm.

*Form.*—Ovoid.

*Base.*—Usually rounded, varies from rounded to flat.

*Apex.*—Normally rounded, some stones slightly pointed.

*Surface.*—Slightly pitted throughout, a small narrow groove on each side of suture.

*Sides.*—Unequal, one side extends further from suture plane.

*Ridges.*—A very small ridge on each side of suture, extends from base to apex.

*Tendency to split.*—None.

*Color.*—10YR 8/4.

Kernel:

*Size.*—Medium. Average length 17.2 mm. Average width 8.9 mm. Average depth 5.4 mm.

*Shape.*—Ovoid.

*Viability.*—Viable, complete embryo development.

*Skin color.*—Varies from 2.5Y 8.5/4 to 5Y 9/4.

Use: Dessert.

*Market*—Local and long distance.

Keeping quality: Good, held firm in storage for 2 weeks at 38° to 42° F. without internal breakdown of flesh, shriveling or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct interspecific tree, substantially as illustrated and described.

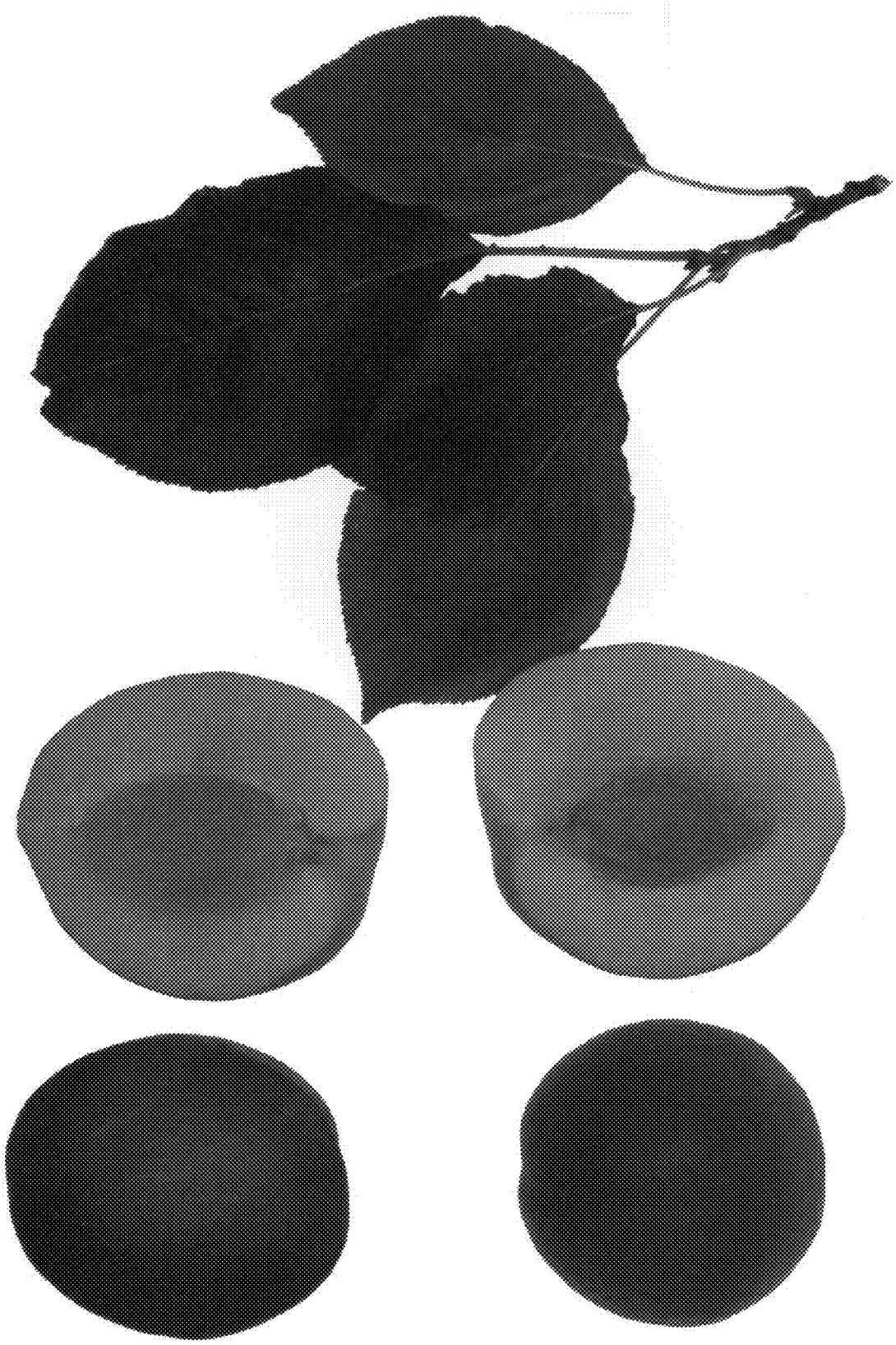

* * * * *